US006943355B2

(12) United States Patent
Shwartz et al.

(10) Patent No.: US 6,943,355 B2
(45) Date of Patent: Sep. 13, 2005

(54) SPECT GAMMA CAMERA

(75) Inventors: Shoulamit C. Shwartz, Atlit (IL); Israel Ohana, Haifa (IL)

(73) Assignee: U.C.G. Technologies, Nesher (IL)

( * ) Notice: Subject to any disclaimer, the term of this patent is extended or adjusted under 35 U.S.C. 154(b) by 139 days.

(21) Appl. No.: 10/333,947

(22) PCT Filed: Aug. 8, 2001

(86) PCT No.: PCT/IL01/00730

§ 371 (c)(1),
(2), (4) Date: Jan. 22, 2003

(87) PCT Pub. No.: WO02/12918

PCT Pub. Date: Feb. 14, 2002

(65) Prior Publication Data

US 2003/0208117 A1 Nov. 6, 2003

(30) Foreign Application Priority Data

Aug. 10, 2000 (IL) .............................................. 137821

(51) Int. Cl.⁷ .............................................. G01T 1/164
(52) U.S. Cl. ................................................. 250/363.04
(58) Field of Search ...................... 250/363.02, 363.04; 378/4, 21

(56) References Cited

U.S. PATENT DOCUMENTS

| H012 H | * | 1/1986 | Bennett et al. | ........ | 250/363.09 |
|---|---|---|---|---|---|
| 5,448,073 A | * | 9/1995 | Jeanguillaume | ........ | 250/363.02 |
| 5,587,585 A | * | 12/1996 | Eisen et al. | ............ | 250/370.09 |
| 5,841,140 A | | 11/1998 | MC Croskey et al. | | |
| 6,028,313 A | * | 2/2000 | McDaniel | .............. | 250/370.09 |
| 6,040,580 A | * | 3/2000 | Watson et al. | ......... | 250/363.03 |
| 6,242,743 B1 | | 6/2001 | De Vito et al. | | |

OTHER PUBLICATIONS

C.E. Metz, F.B. Atkins and R.N. Beck, "The Geometric transfer function component for scintillation camera collimators with straight parallel holes," Phys. Med. Biol., 1980, v. 25, p. 1059–1070.

D.L. Bailey, B.F. Hutton & P.J. Walker, "Improved SPECT Using Simultaneous Emission and Transmission Tomography", J Nucl Med, 1987, 28: 844–851.

L. A. Shepp and Y. Vardi, "Maximum likelihood reconstruction for emission tomography," IEEE Trans Med. Imaging, 1982, v. 1, p. 113–122.

(Continued)

Primary Examiner—Constantine Hannaher
(74) Attorney, Agent, or Firm—Shalom Wertsberger Saltamar Innovations

(57) ABSTRACT

A method and apparatus of obtaining and reconstructing an image of a portion of a body, administered by a radiopharmaceutical substance, by using Single-photon emission computerized tomography (SPECT) for determination of functional information thereon. The method comprises (a) acquiring gamma ray photons emitted from said portion by means of a detector capable of converting the photons into electric signals, the detector having at least one crystal and allowing said gamma rays having incident angles essentially exceeding 5 degrees and, preferably, exceeding 10 degrees to be detected; (b) processing said electric signals by a position logic circuitry and thereby transforming them into data indicative of positions on said photon detector crystal, where the photons have impinged the detector; and (c) reconstructing an image of a spatial distribution of the pharmaceutical substance within the portion of the body by processing said data and taking into consideration weight values which are functions of angles and, possibly, distances between different elements of the portion of the body and corresponding elements of this position's projection on the detector.

19 Claims, 5 Drawing Sheets

OTHER PUBLICATIONS

K. Lange and R. Carson, "EM reconstruction Algorithms for emission and Transmission tomography," J. Comput. Assist. Tomogr., 1984, v. 8, p. 306–316.

P.J. Green, Bayesian Reconstructions from emission tomography data using a modified EM algorithm, IEEE Trans Med. Imaging, 1990, v. 9, p. 84–93.

P.J. Green, On the use of the EM algorithm for penalised likelihood Estimation J. Roy. Statist. Soc. (B), 1990, 52:443–452.

D. German and G. Reynolds, Constrained Restoration and the Recovery of Discontinuities, IEEE Transactions on Pattern Analysis and Machine Intelligence, 1992, v. 14, p. 367–383.

* cited by examiner

SPECT GAMMA CAMERA

FIELD OF THE INVENTION

This invention relates to Nuclear Medicine, and, more particularly, to Single-photon emission computerized tomography (SPECT) imaging technique.

BACKGROUND OF THE INVENTION

SPECT is one of Nuclear Medicine imaging techniques that enable to acquire functional information about patient's specific organ or body system. This functional information is attained from analysis of internal radiation obtained from pharmaceutical substance administered to the patient, which is labeled with a radioactive isotope. The radioactive isotope decays, resulting in the emission of gamma rays, thus providing with information on the concentration of the radiopharmaceutical substance introduced to the patient's body. An instrument for the detection of gamma ray emissions of the radiopharmaceutical substance administered in the body is known as gamma camera. The SPECT technique collects gamma ray photons that are emitted from the patient and reconstructs an image or a series of images of the place in the body from which the gamma rays are originated. From this picture a physician can determine how a particular organ or system is functioning. The main components making up a conventional gamma camera are a collimator for passing therethrough gamma rays to be detected, photon detector crystal or detector array, position logic circuits and data analysis computer. Depending on the type of the detector crystal, conventional gamma camera may or may not include a photo-multiplier tube array.

A gamma ray photon that has passed through the collimators, interacts with the detector crystal by means of the Photoelectric Effect or Compton Scattering with ions of the crystal. These interactions cause the release of electrons which in turn interact with the crystal lattice to produce light, in a process known as scintillation. Since only a very small amount of the light is given off from the crystal, photo-multiplier tubes are normally attached to the back of the crystal. Typically, such conventional gamma camera has several photo-multiplier tubes arranged in a geometrical array. The position logic circuits that follow the photo-multiplier tube array, receive the electrical impulses from the tubes and determine where each scintillation event occurred in the detector crystal. Finally, in order to deal with the incoming projection data and to process it into a readable image of the spatial distribution of activity within the patient, a processing computer is used. The computer may use various different methods to reconstruct an image.

Different collimators are used in gamma cameras to limit the detection of photons to incidence range of predetermined angles. A parallel-hole collimator is usually made from lead or tungsten and has thousands of straight parallel holes in it, allowing only those gamma rays traveling along certain directions to reach the detector. As a result of that, the ratio of emitted, versus detected, photons may reach 10000 to 1. In order to decrease this ratio, converging or diverging hole collimators, for example, fan-beam and cone-beam are also known in the art. The usage of these collimators increases the number of photon counts, which improves sensitivity. The sensitivity, however, is inversely related to geometric resolution, which means that improving collimator resolution decreases collimator sensitivity, and vice versa.

The current use of collimators results in a rather low detection efficiency of conventional SPECT which leads to prolonged data acquisition time and the need to administer high dosage of the radiopharmaceutical substance.

SUMMURY OF THE INVENTION

The general object of the present invention, which will be described subsequently in greater detail, is to provide a novel technique for acquisition and reconstruction of SPECT images obtained by a gamma camera.

The technique of the present invention enables the gamma camera to accept gamma rays at the incident angles in the range of up to 90 degrees, e.g. to work when the gamma rays are non-collimated, whilst in the conventional way of acquisition and reconstruction of SPECT images, gamma rays having incident angles exceeding 2–4 degrees are normally not detected.

The present invention is based on a correct account of the directions of the gamma rays, achieved by taking into consideration weight values which establish coupling between different parts of the examined organ and the corresponding parts of the organ's projection on the detector. For example, the weight values might be chosen as a function of angles at which each element of the detector is viewed from different points of the corresponding imaged area of the organ.

There is provided in accordance with the present invention, a method of obtaining and reconstructing an image of a portion of a body, administered by a radiopharmaceutical substance, by using SPECT for determination of functional information thereon, comprising the steps of:

(a) acquiring gamma ray photons emitted from said portion by means of a detector capable of converting the photons into electric signals, the detector having at least one crystal and allowing said gamma rays having incident angles essentially exceeding 5 degrees and, preferably, exceeding 10 degrees to be detected;

(b) processing said electric signals by a position logic circuitry and thereby transforming them into data indicative of positions on said photon detector crystal, where the photons have impinged the detector; and (c) reconstructing an image of a spatial distribution of the pharmaceutical substance within the portion of the body by processing said data and taking into consideration weight values which are functions of angles and, possibly, distances between different elements of the portion of the body and corresponding elements of this position's projection on the detector.

The technique of the present invention may lead to substantial improvement in image resolution (better than 7 mm) and improvement in image sensitivity with respect to the conventional SPECT technique. That may result in better lesion detectability, shorter acquisition time and administration of smaller doses of radiopharmaceutical substances to the patient.

BRIEF DESCRIPTION OF THE DRAWING

In order to understand the invention, its operating advantages and to see how it may be carried out in practice, preferred embodiments will now be described, by way of a non-limiting examples only, with reference to the accompanying drawings, in which.

DETAILED DESCRIPTION OF EMBODIMENTS

Figure 1:
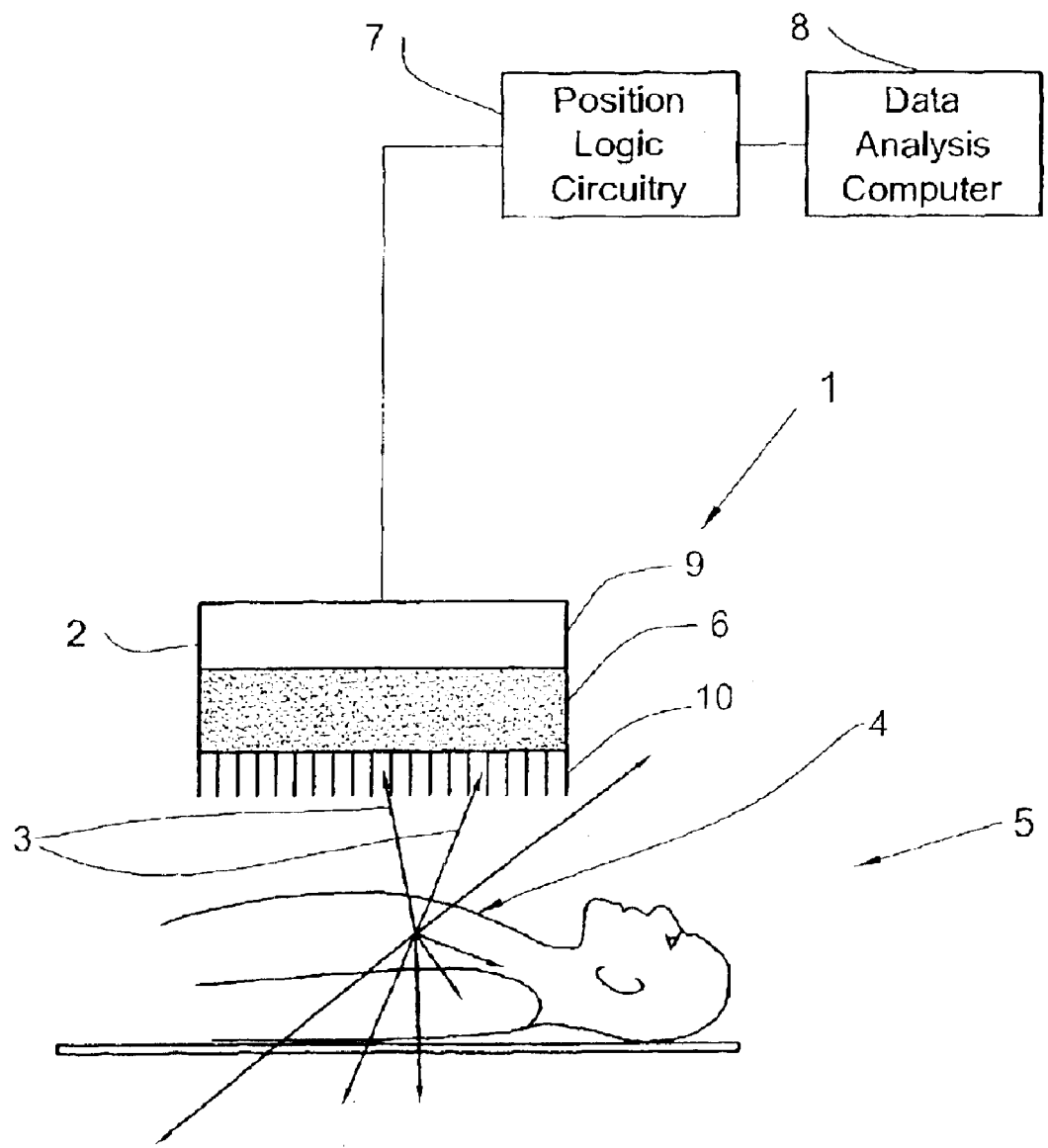
FIG. 1 is a pictorial illustration of the operation of a gamma camera in accordance with the present invention.

Reference first is made to FIG. 1 depicting a side view of a simplified schematic diagram of gamma camera in accordance with the present invention, for obtaining a SPECT image of a portion of a body that has been administered by a radiopharmaceutical substance which radiates gamma rays.

The gamma camera 1 comprises a detector 2 mounted above an inspected portion 4 of a body 5, a position logic circuitry 7 and a data analysis computer 8, all connected appropriately.

Detector 2 includes at least one photon detector crystal 6 facing the portion 4 of body 5. The photon detector crystal 6 may be in the form of a semiconductor crystal or crystals. This crystal(s) may be selected from a first group including Cadmium-Telluride (CdTe), Cadmium-Zinc-Telluride (CeZnTe), Lead Iodine (PbI).

The detector 2 of the gamma camera 1 may further include at least one photo-multiplier 9. The photon detector crystal(s) in this case may be selected from a second group including Sodium Iodine (NaI), Bismuth Germanate (BGO), Yttrium Oxyorthosilicate (YSO), Cerium-doped Lutetium Oxyorthosilicate (LSO) and Cesium-Iodine (CsI) with solid state photo-diode or avalanche photo-diode (APD).

The detector crystals listed above have different characteristics that are relevant for SPECT imaging: they differ in their ability to resolve photon energy (also termed "energy resolution"), their internal spatial resolution and their stopping power. All of these characteristics affect the resolution and sensitivity of the resultant images. Therefore, SPECT cameras utilizing different detector crystals will yield different resolution, using the same reconstruction algorithm.

Detector 2 may also be in the form of an array of photon detector crystals arranged in at least one row. The photon detector crystal array may be in the form of a plane or a ring surrounding the portion of the body. For example, detector 2 may be of the kind used in a known per se Anger camera.

Detector 2 may be capable of rotating around, or moving along, a desired trajectory relative to the body to acquire data at multiple predetermined positions from multiple views around the body.

Angles of incidence of gamma rays from the portion 4 of the body 5 may be in the range from 0° to 90°. Detector 2 may be provided with means 10 establishing angles of incidence of gamma rays on the detector in a restricted range. It is noted that by angle of incidence it is meant the angle between the perpendicular to the surface of the detector and the ray path.

Such means may be in the form of appropriate collimators. However, these means should be such as to allow the gamma rays having various incident angles in the range of 0 to 5 or more degrees, and preferably, in the range of 0 to 10 or more degrees, to be detected. The collimator holes may be symmetric, such as circular or hexagonal shaped holes, or have different dimensions along the different axis, such as ellipse or rectangular shape holes. Furthermore, the shape of the bore of the collimators may be cylindrical, conic or other converging shapes.

Figure 3:
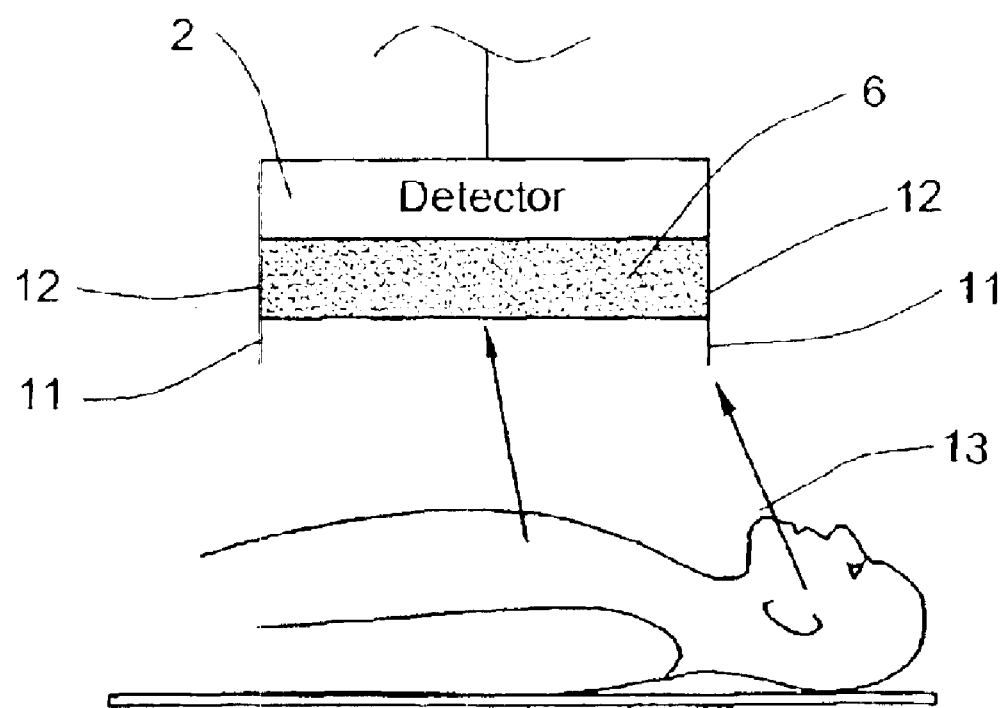
FIG. 3 is a pictorial illustration of an alternative embodiment of a gamma camera according to the present invention.

Alternatively, when no collimators are used, rows or columns of septa may be used for limiting the number of beams impinging the detector, to beams coming from certain directions. For limiting the field of view of the entire detector 2, at least one septum 11 may be mounted at detector 2 along one of its axes (FIG. 3), however it is recommended to use at least two, mounted at opposite edges. The septa are designed to avoid the penetration of gamma rays 13 emanating from outside the field of view and thereby decrease a computational load.

In operation, detector 2 acquires radioisotope gamma ray photons 3, which are emitted from portion 4 of body 5 and passing through means 10. The gamma photons impinge the photon detector crystal 6. If the crystal 6 is a semiconductor crystal selected from the first group specified above, then the crystal converts the photons into electric signals, which are fed into a position logic circuitry 7 for processing. Alternatively, if the crystal is selected from the second group specified above, i.e. is of the kind that utilizing photo-multipliers, then the crystal converts photons 3 into scintillation light, which is, thereafter, transformed into electric signals by photo-multiplier 9.

As a result of the processing, the electric signals are transformed into data indicative of photon energy and positions on the photon detector crystal 6 in which the photons impinge the detector. The data that includes the position at which each photon impinged the detector, for each position of the detector, is termed projection. Thereafter, the projections are fed into a data analysis computer 8 for the purpose of reconstructing an image of a spatial distribution of the pharmaceutical substance within the portion of the body by processing said data. The photon energy information is registered for the assessment of the amount of Compton scattering that is introduced in the acquisition. In general, there is one energy window around each peak of the radio-pharmaceutical substance. The width of each window is preferably set as narrow as may be reasonable to the specific detector that is used, in order to reject as many scattered photons as possible.

The reconstruction of the image according to the present invention may be performed based on any appropriate existing algorithm, however, it should necessarily be based on weight values, which are functions of either angles or angles and distances between different elements of the portion of the body and corresponding elements of body's projection on the detector.

For example, the reconstruction of the image may start from dividing an area of the detector facing the body onto M bins and dividing portion 4 of body 5 onto N voxels. As a result of such discretization, the photons are binned according to their position on the detectors and a set of values $D_{ik}$ (wherein i=1, . . . , M) indicative of a number of photons acquired by the i-th bin, for any position k (wherein k=1, . . . , L) at which the detectors are positioned while acquiring this data, is provided. Clearly, if the detector includes M crystals and each crystal is associated with a bin, then the step of additionally dividing of the detector's area onto M bins is unnecessary.

Further, a coupling between each bin of the detector at each position k at which the detectors are positioned while acquiring this data, and each voxel of the portion of the body is established. As a result of the coupling, a matrix $P=\{P_{ijk}\}$ of weight values of the voxels of the portion of the body (wherein i=1, ..., M, j=1, ..., N and k=1, ..., L) is constructed. For the rest of the discussion, the reference to the position k in the elements of the matrix P, and in the detector values D will be omitted.

Figure 2A:
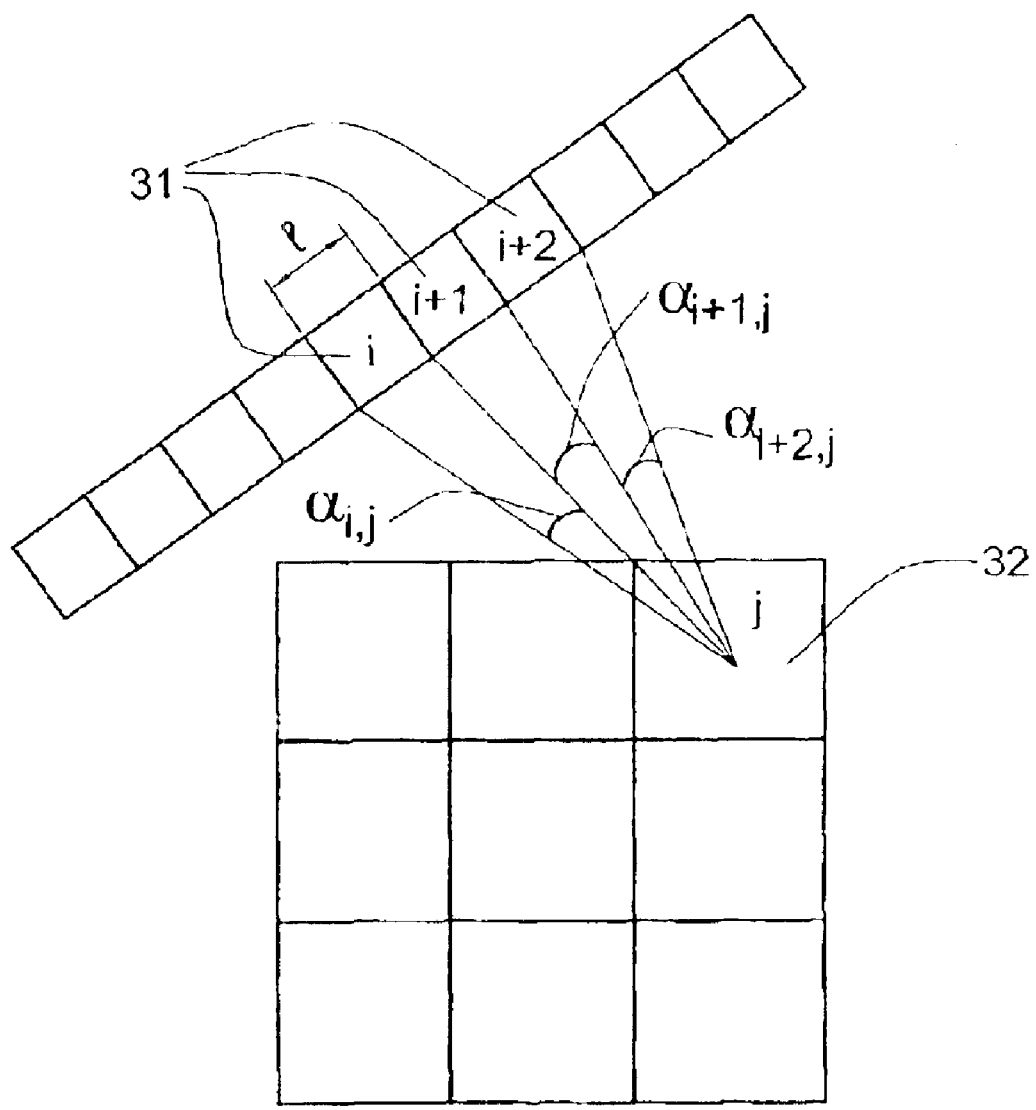
FIG. 2a is a simplified diagram depicting one example of the coupling between different elements of the detector and corresponding elements of the body in accordance with the present invention.

FIG. 2a shows a simplified, two dimensional diagram depicting one example of the coupling between bins 31 having indices i, i+1, i+2, ... and a voxel 32 having an index j, which results in weight values $P_{ij}$, $P_{i+1j}$, and $P_{i+2j}$ that are functions of a set of angles $\alpha_{ij}$, $\alpha_{i+1j}$, $\alpha_{i+2j}$, ..., and possibly distances between the bins 31 and voxel 32. In the case when collimators are used, a photon that emanated from voxel i and is within the angle of view of a given bin, may be absorbed by the walls of the collimator at that area. Therefore, the $P_{ij}$ should be multiplied by the relative effective area of bin i as viewed from voxel j. (see, for example, C. E. Metz, F. B. Atkins and R. N. Beck, "*The Geometric transfer function component for scintillation camera collimators with straight parallel holes*," Phys. Med. Biol., 1980, v. 25, p. 1059–1070).

According to a more general example, P may be a matrix in which each of the matrix elements $P_{ij}$ is a function of an average angle and possibly distance at which a detector bin having an index i is viewed from the voxel having an index j. Alternatively, the P may be a matrix in which each of the matrix elements $P_{ij}$ is a function of an angle and possibly distance at which the detector bin having an index i is viewed from a center of the voxel having an index j.

Figure 2B:
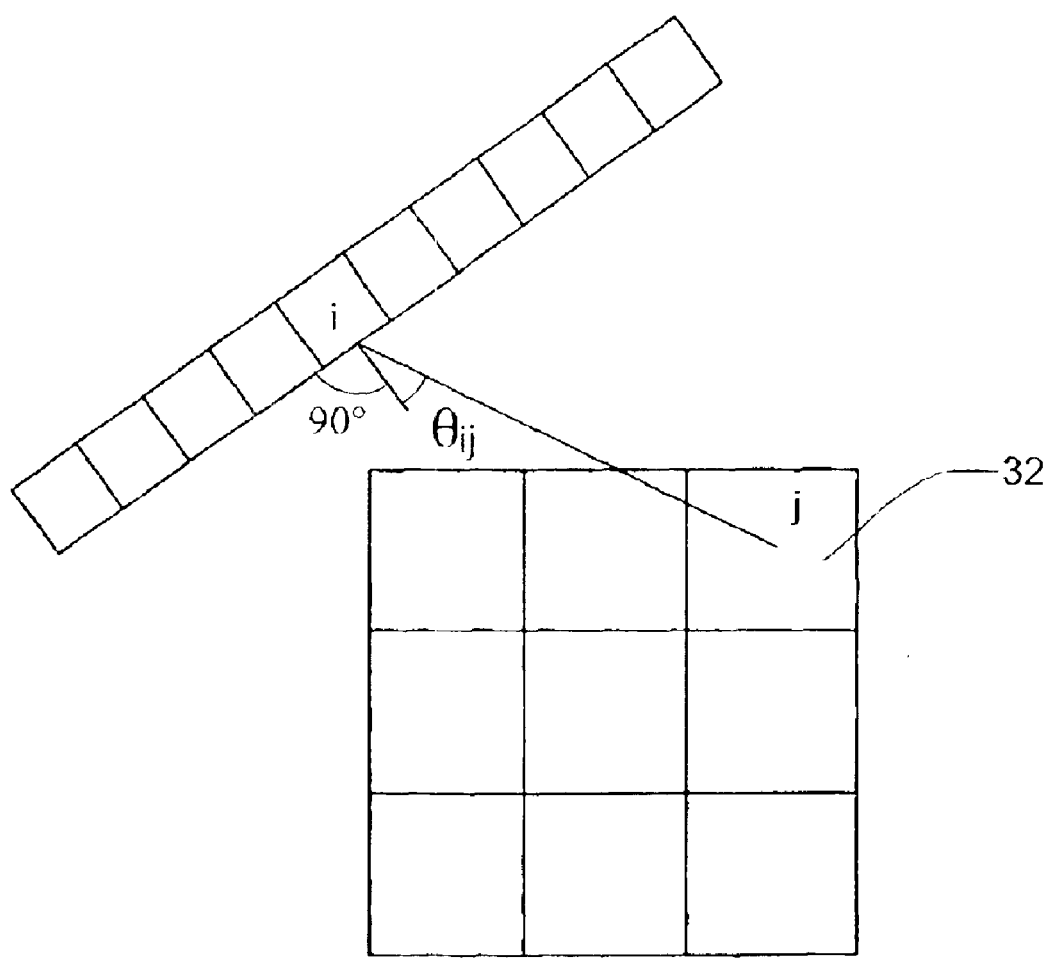
FIG. 2b is a simplified diagram depicting another example of the coupling between different elements of the detector and corresponding elements of the body in accordance with the present invention.

FIG. 2b illustrates another example, in 2 dimensions, wherein P is a matrix in which its elements are presented by equation $$P_{ij} = c\frac{l\cos\Theta_i}{z^2},$$

wherein $\Theta_i$ is the angle at which the detector's bin having an index i views the voxel having an index j, c is a constant, l is the length of the detector bin's side, z is the distance between the centers of the voxel having index j and the bin having index i. As yet another example, the value of the angle $\Theta_i$ may be an average angle of view from the bin having an index i into the voxel having an index j.

In the most general case, the three dimensional case, the weights depend on the solid angle between a given point in a voxel and a given detector bin, on the position k of the detector relative to the starting point of the acquisition and on the distance of the voxel from the bin. As with the two-dimensional case, when collimators are used, these weights are multiplied by the relative effective area of the bin associated with that solid angle.

The elements of the matrix P may be modified to incorporate the attenuation effect, when attenuation map is available. The modification is such that the $P_{ij}$ as described above, will take into account the attenuation terms that are associated with the voxels through which the ray emanated at voxel j pass to arrive at bin i, when the detectors are in position k. (see, for example, D. L. Baiely, B. F. Hutton & P. J. Walker, "*Improved SPECT Using Simultaneous Emission and Transmission Tomography*", J Nuc Med, 1987, 28: 844–851).

In order to derive voxel values $V_j$ of an image of the portion of the body and thereby to obtain a spatial distribution of the pharmaceutical substance indicating the functional information on this portion of the body, a mathematical model should be formulated and solved. Formulation of the mathematical model includes modeling a relation between the set of values $D_i$ and a set of unknown voxel values $V_j$ of the image.

As one example, the mathematical problem for deriving $V_j$ may be formulated as a set of algebraic equations $$D_i = \sum_{j=1}^{N} P_{ij}V_j$$

with respect to each unknown value $V_j$ may be solved, wherein j=1, ..., N and i=1, ..., M. As it can be clear to a man of the art, the set of equations in a general form is:

$$D_i = \sum_{j=1}^{N} P_{ij}V_j + E_i,$$

i.e. also includes a set of measurement errors $E_i$.

As another example, the mathematical problem may be formulated as an optimization problem with a likelihood function that should be solved for deriving the unknown values $V_j$ (see, for example, the technique of L. A. Shepp and Y. Vardi, "*Maximum likelihood reconstruction for emission tomography*," IEEE Trans Med. Imaging, 1982, v. 1, p. 113–122, or K. Lange and R. Carson, "*EM reconstruction algorithm for emission tomography*," J. Comput. Assist. Tomogr., 1984, v. 8, p. 306–316).

The optimization problem is formulated as a statistical model of the emission process for estimating image data. According to the model, the number of photons $V_j$ that are emitted from a voxel with an index j obeys the Poisson distribution $$P(V_j = n) = \frac{e^{-\lambda(V_j)}\lambda(V_j)^n}{n!},$$

wherein $P(V_j=n)$ is the probability of having n events of photon emissions in the j-th voxel, and $\lambda(V_j)$ is the unknown mean value of the Poisson distribution. Further, the number of photons $D_i$ that are acquired by the i-th bin also obeys the Poisson distribution with mean value of the distribution $\lambda(D_i)$. The random variables $V_j$ and $D_i$ as well as their respective mean values $\lambda(V_j)$ and $\lambda(D_i)$ are, correspondingly, related via the following equations $$D_i = \sum_{j=1}^{N} P_{ij}V_j \text{ and } \lambda(D_i) = \sum_{j=1}^{N} P_{ij}\lambda(V_j).$$

Thus the optimization problem is used to estimate the mean value $\lambda(V_j)$ of the Poisson random variables $V_j$, using the $D_i$ values measured by the detector. For example, one conventional statistical approach for determination of $V_j$ is to find a maximum of the likelihood function $$L[\lambda(D_i)] = \prod_{i=1}^{M} \frac{e^{-\lambda(D_i)}\lambda(D_i)^{D_i}}{D_i!},$$

with respect to the unknowns $V_j$.

An image of the portion of the body reconstructed by utilizing the algorithms described above may be a two dimensional image or a three dimensional image of the portion of the body.

As yet another example, the mathematical problem may be formulated as a Bayesian optimization problem, in which a likelihood function is utilized together with a penalty function known per se. (See for example, P. J. Green, *Bayesian reconstruction from emission tomography data using a modified EM algorithm*, IEEE Trans Med. Imaging, 1990, V. 9, p. 84–93, or P. J. Green, *On the use of the EM algorithm for penalised likelihood estimator*, J. Roy. Statist. Soc. (B), 1990, 52:443–452, or D. Geman and G. Reynolds, *Constraint Restoration and the Recovery of Discontinuities*, IEEE trans on Pattern Analysis and Machine Intelligence, 1992, v. 14, p. 367–383.) This optimization problem should be solved for deriving the unknown values $V_j$. As an example, but not limited to, a general form of the Bayesian optimization problem can be written as follows:

$$V=arg\ max\{L[\lambda(D_i)]+\alpha F(V_j,V_k)\},$$

where $\alpha$ is the weight that is given to the prior function F.

For instance the penalty function may be chosen in the form of $$F(V_j, V_k) = \sum_{j,k} (V_j - V_k)^2,$$

wherein the sum is taken over two neighboring voxels having indices j and k. Such a penalty function expresses some prior knowledge about the smoothness characteristics of the reconstructed image. Other penalty functions, which preserve discontinuities are more adequate for SPECT reconstruction.

As it can be clear to, a man of the art, the choice of the optimal minimal incidence angle utilized for a scan, is guided by the trade-offs between resolution and sensitivity that can be tolerated. Factors, for instance, such as desired acquisition time, resolution, sensitivity, noise characteristics should also be taken into account. This choice dictates whether to use collimators, if so what are their characteristics, or alternatively use septa or do not use collimators at all. When using collimators for example, the characteristics of the collimator, such as the hole dimensions, are determined by the accepted incidence angle, as well as by other factors. The accepted incidence angle itself is determined by the desired resolution and sensitivity. Hence, practical solutions will depend on the factors mentioned above and can be optimized accordingly. For example, in cardiac imaging, the collimator characteristics are guided by the priority to have a high sensitivity image rather than high resolution one, whereas for brain perfusion images, because of the brain's fine structures, high resolution is required.

Figure 4A:
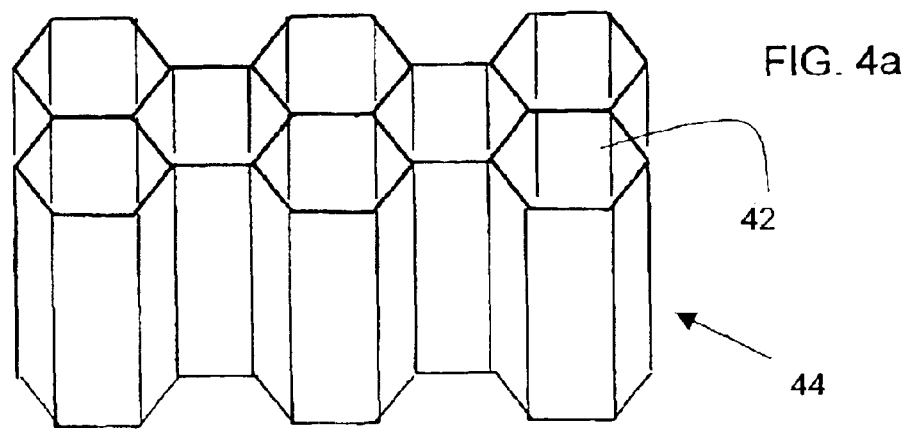
FIG. 4a illustrates a portion of a collimator to be used in a preferred embodiment of a gamma camera in accordance with the present invention, having hexagonal holes arranged in a beehive arrangement.

FIG. 4*a* illustrates a portion of a collimator to be used in a preferred embodiment of a gamma camera in accordance with the present invention, having hexagonal holes arranged in a beehive arrangement. The collimator 44, is arranged in a beehive configuration of hexagonal holes 42.

Figure 4B:
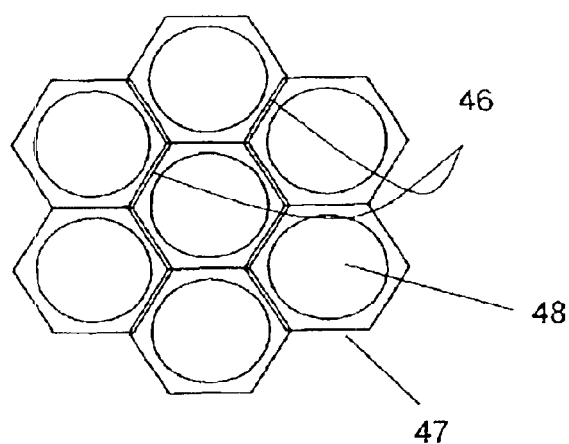
FIG. 4b illustrates a front-view of a portion of a collimator to be used in another preferred embodiment of a gamma camera in accordance with the present invention, having circular holes arranged in a beehive arrangement, and separating septa.

FIG. 4*b* illustrates a portion of a collimator to be used in another preferred embodiment of a gamma camera in accordance with the present invention, having circular holes arranged in a beehive arrangement, and separating septa. In this embodiment the collimator consists of hexagonal cells 47, each cell having a circular hole 48 defined by the walls 46.

Figure 4C:
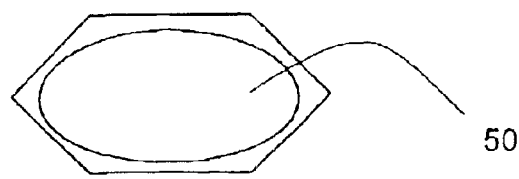
FIG. 4c illustrates an alternative collimator hole having oval shape.

FIG. 4*c* illustrates an alternative collimator hole having oval shape 50. The collimator holes may be symmetric, such as circular, square or hexagonal shaped holes. Alternatively the collimator holes may be non-symmetric. The collimator holes may be of different dimensions along different axes, such as ellipse or rectangular shape holes, and these holes may have cylindrical, conic or other converging or diverging shapes. In an alternative embodiment of the camera of the present invention, the camera is provided with a collimator having direction bias holes favoring detection from a predetermined lateral direction and limiting detection from other directions.

As such, those skilled in the art to which the present invention pertains can appreciate that while the present invention has been described in terms of the above examples, the conception upon which this disclosure is based, may readily be utilized as a basis for the designing of other structures, methods and systems for carrying out the purposes of the present invention.

It should be noted that the scope of the invention is not to be construed as limited by the illustrative examples set forth herein, but is to be determined in accordance with the appended claims.

What is claimed is:

1. A method of obtaining and reconstructing an image of a portion of a body, administered by radiopharmaceutical substance radiating gamma rays, by using SPECT (single photon emission computerized tomography), for determination of functional information thereon, comprising the steps of:

(a) acquiring photons emitted from said portion of the body, by means of a detector capable of converting the photons into electric signals, the detector having at least one crystal and adapted to detect emitted photons having incident angles in the range og 0 to 5 degrees;

(b) processing said electric signals by a position logic circuitry and thereby deriving therefrom data indicative of positions on said photon detector crystal, where the photons have impinged the detector; and (c) reconstructing an image of a spatial distribution of the pharmaceutical substance within the portion of the body by processing said data in conjunction with weight values, derived from functions of either solid angles or solid angles and distances between different discrete elements of the portion of the body and corresponding discrete elements of the projection of the portion of the body on the detector;

wherein said reconstructing an image by processing said data comprises the steps of:

(a) dividing an area of the detector facing the body into M bins;

(b) dividing the portion of the body into N voxels;

(c) providing a set of values $D_i$ (wherein i=1, . . . , M) reflective of the number of photons acquired by each bin;

(d) constructing a matrix P having matrix elements $P_{ij}$ of weight values of the voxels of the portion of the body (wherein i=1, . . . , M and j=1, . . . , N), the matrix P setting a relation between each bin of the detector each voxel of the portion of the body;

(e) modeling a relation between said set of values $D_i$ and a set of voxel values $V_j$ of said image and deriving said set of voxel $V_j$ of said image, whereby said spatial distribution of the pharmaceutical substance indicating the functional information on said portion of the body is obtained.

2. The method of claim 1 wherein the step of modeling a relation between said set of values $D_i$ and a set of voxel values $V_j$ of said image and deriving said set of voxel values $V_j$ of said image comprises the step of solving a set of equations $$D_i = \sum_{j=1}^{N} P_{ij} V_j$$

with respect to each value $V_j$, (wherein i=1, ..., M).

3. The method of claim 1 wherein the step of modeling a relation between said set of values $D_i$ and a set of voxel values $V_j$ of said image and deriving said set of voxel values $V_j$ of said image comprises the step of solving a set of equations $$D_i = \sum_{j=1}^{N} P_{ij} V_j + E_i$$

with respect to each value $V_j$, wherein $E_i$ is a set of measurement errors.

4. The method of claim 1 wherein the step of modeling a relation between said set of values $D_i$ and a set of voxel values $V_j$ of said image and deriving said set of voxel values $V_j$ of said image comprises the step of solving an optimization problem for estimating a mean value $\lambda(V_j)$ of Poisson random variables $V_j$, using the $D_i$ values measured by the detector.

5. The method of claim 4, wherein estimating the value $\lambda(V_j)$ of the Poisson random variables $V_j$, is carried out by calculating a maximum of the likelihood function $$L[\lambda(D_i)] = \prod_{i=1}^{M} \frac{e^{-\lambda(D_i)} \lambda(D_i)^{D_i}}{D_i!},$$

with respect to the unknowns $V_j$.

6. The method of claim 1 wherein the step of modeling a relation between said set of values $D_i$ and a set of voxel values $V_j$ of said image and deriving said set of voxel values $V_j$ of said image comprises the step of solving a Bayesian optimization problem utilizing a likelihood and penalty functions.

7. The method of claim 6, wherein the Bayesian optimization problem has the general form $V = \text{argmax}\{L[\lambda(D_i)] + \alpha F(V_j, V_k)\}$, where $\alpha$ is the weight that is given to the penalty function F.

8. The method of claim 1 wherein the matrix P is matrix in which each of the matrix elements $P_{ij}$ is a function of an average distance and solid angle at which detector bin having an index i is view from the voxel having an index j.

9. The method of claim 1 wherein the matrix P is a matrix in which each of the matrix elements $P_{ij}$ is a function of an average solid angle at which a detector bin having an index i is viewed from the voxel having an index j.

10. The method of claim 1 wherein the matrix P is a matrix in which each of the matrix elements $P_{ij}$ is a function of an average distance and solid angle at which a voxel having an index j is viewed from a detector bin having an index i.

11. The method of claim 1 wherein the matrix P is a matrix in which each of the matrix elements $P_{ij}$ is a function of an average solid angle at which a voxel having an index j is viewed from a detector bin having an index i.

12. The method of claim 1 wherein the matrix P is a matrix in which each of the matrix elements $P_{ij}$ is a function of a solid angle and distance at which a detector bin having an index i is viewed from a center of a voxel having an index j.

13. The method of claim 1 wherein the matrix P is a matrix in which each of the matrix elements $P_{ij}$ is a function of a solid angle at which a detector bin having an index i is viewed from a center of a voxel having an index j.

14. The method of claim 1 wherein the matrix P is a matrix in which each of the matrix elements is a function of a solid angle and distance at which a center of a voxel having an index j is viewed from a detector bin having an index i.

15. The method of claim 1 wherein the matrix P is a matrix in which each of the matrix elements $P_{ij}$ is a function of a solid angle at which a center of a voxel having an index j is viewed from a detector bin having an index i.

16. The method of claim 1 wherein the modeling of the relation between said set of values $D_i$ and a set of voxel values $V_j$ of said image, is biased by an attenuation effect of the patient body.

17. The method of claim 16 wherein the matrix P is a matrix in which each of the matrix elements $P_{ij}$ is influenced by the attenuation density that exists on the path of the photons that emanate at voxel j and arrive at bin i, for each detector position k.

18. The method of claim 16 wherein the matrix P is a matrix in which each of the matrix elements $P_{ij}$ is influenced by the attenuation density that exists on the path of the photons that emanate at voxel j and arrive at bin i, for each detector position k and for each energy peak of the radio-pharmaceutical substance that is used.

19. The method of claim 1, further comprising the step of providing a a collimator between said portion of body and said detector, and wherein the matrix P is a matrix in which each of the matrix elements $P_{ij}$ is multiplied by the relative effective area of bin i associated with the solid angle between voxel j and bin I.

* * * * *

UNITED STATES PATENT AND TRADEMARK OFFICE
CERTIFICATE OF CORRECTION

PATENT NO. : 6,943,355 B2 Page 1 of 1
APPLICATION NO. : 10/333947
DATED : September 13, 2005
INVENTOR(S) : Shwartz et al.

It is certified that error appears in the above-identified patent and that said Letters Patent is hereby corrected as shown below:

In Col. 8, line 42, replace "og" with --of--;
In Col. 8, line 42, insert --more than-- after "0 to"

Signed and Sealed this

Twenty-sixth Day of June, 2007

JON W. DUDAS
*Director of the United States Patent and Trademark Office*